United States Patent [19]

Golden et al.

[11] Patent Number: 4,573,469
[45] Date of Patent: Mar. 4, 1986

[54] TWO-PIECE TISSUE FASTENER WITH COINABLE LEG STAPLE AND RETAINING RECEIVER AND METHOD AND INSTRUMENT FOR APPLYING SAME

[75] Inventors: Donald M. Golden, Cherry Hill, N.J.; William P. McVay, Clearwater, Fla.

[73] Assignee: Ethicon, Inc., Somerville, N.J.

[21] Appl. No.: 506,151

[22] Filed: Jun. 20, 1983

[51] Int. Cl.⁴ ............................................. A61B 17/04
[52] U.S. Cl. ........................ 128/334 C; 227/DIG. 1; 411/469; 411/363
[58] Field of Search ........... 128/346, 337, 335, 334 R, 128/334 C, 330, 325, 326, 92 B; 3/1; 227/DIG. 1, 15-18, 77; 411/469, 451, 360, 501, 506, 362-364, 455-457; 24/543, 518, 614, 623, 703, 297, 150 FP, 16 PB, 697, 580-581, 584, 453, 30.5 P, 737, 515, 513, 503, 94-96

[56] References Cited

U.S. PATENT DOCUMENTS

| | | | |
|---|---|---|---|
| Re. 27,391 | 6/1972 | Merser | 24/150 FP X |
| 306,479 | 10/1884 | Goddard | 24/95 |
| 389,660 | 9/1888 | Mandel et al. | 411/457 X |
| 579,831 | 3/1897 | Ketchum | 24/95 |
| 1,988,233 | 1/1935 | Berendt | 24/95 |
| 2,794,981 | 6/1957 | Brayton | 227/15 |
| 2,881,762 | 4/1959 | Lowrie | 128/337 |
| 2,897,561 | 8/1959 | Megibow | 24/95 |
| 2,900,696 | 8/1959 | Bacon | 24/614 X |
| 3,009,852 | 11/1961 | Gruner | 128/330 X |
| 3,166,072 | 1/1965 | Sullivan | 128/346 X |
| 3,210,820 | 10/1965 | Humiston | 24/584 X |
| 3,326,217 | 6/1967 | Kerr | 227/DIG. 1 C X |
| 3,357,296 | 12/1967 | Lefever | 128/334 C X |
| 3,494,006 | 2/1970 | Brumlik | 411/456 X |
| 3,570,497 | 3/1971 | Lemole | 128/335.5 |
| 3,577,601 | 5/1971 | Mariani et al. | 24/16 |
| 3,683,927 | 8/1972 | Noiles | 128/326 X |
| 3,744,495 | 7/1973 | Johnson | 128/330 |
| 3,802,438 | 4/1974 | Wolvek | 128/335 |
| 3,857,396 | 12/1974 | Hardwick | 128/335 |
| 3,875,648 | 4/1975 | Bone | 227/19 X |
| 3,981,051 | 9/1976 | Brumlik | 411/456 X |
| 4,006,747 | 2/1977 | Kronenthal et al. | 128/337 X |
| 4,038,725 | 8/1977 | Keefe | 24/150 FP |
| 4,060,089 | 11/1977 | Noiles | 128/337 X |
| 4,235,238 | 11/1980 | Ogiu et al. | 128/335 X |
| 4,259,959 | 4/1981 | Walker | 128/337 |
| 4,294,255 | 10/1981 | Geroc | 128/334 C |
| 4,326,531 | 4/1982 | Shimonaka | 128/326 |
| 4,400,833 | 8/1983 | Kurland | 3/1 |
| 4,402,445 | 9/1983 | Green | 128/334 R X |
| 4,454,875 | 6/1984 | Pratt et al. | 128/92 B |

FOREIGN PATENT DOCUMENTS

| | | | |
|---|---|---|---|
| 1097171 | 3/1981 | Canada | 128/330 |
| 1385691 | 12/1964 | France | 40/300 |
| WO83/01190 | 4/1983 | PCT Int'l Appl. | 227/DIG. 1 |
| 82738 | 10/1919 | Switzerland | 128/330 |
| 972731 | 10/1964 | United Kingdom | 128/346 |

Primary Examiner—Michael H. Thaler
Attorney, Agent, or Firm—Robert L. Minier

[57] ABSTRACT

A fastener is provided to hold together separated portions of mammalian tissue and includes an open loop fastening member and a receiver adapted to receive the legs of the fastening member. The legs of the fastening member are then deformed to effect engagement of the fastening member and receiver. An instrument is provided for holding the receiver on one side of the tissue portions and for inserting the fastening member through the tissue portions and into the receiver. The instrument also (1) deforms the legs of the fastening member to effect the engagement of the fastening member with the receiver and (2) severs the protruding portions of the legs.

8 Claims, 29 Drawing Figures

TWO-PIECE TISSUE FASTENER WITH COINABLE LEG STAPLE AND RETAINING RECEIVER AND METHOD AND INSTRUMENT FOR APPLYING SAME

DESCRIPTION

1. Technical Field

This invention relates, in general, to the fastening together of portions of tissue in surgical procedures and is especially advantageous in the surgical closure of internal organ tissue.

2. Background of the Invention

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International patent application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions. The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. Such a fastening device may be fabricated from a biodegradable or absorbable material.

Yet another tissue fastening device having a plurality of components is disclosed in commonly assigned U.S. patent application Ser. No. 349,443, filed Mar. 18, 1982. The fasteners disclosed in that application are made from various polymeric materials and the legs of the U-shaped portion of the fastener have a taper to improve the penetration in the tissue.

Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

Further, it would be beneficial if such an improved fastener had a configuration that would enable the fastener to be fabricated with 1) as small a size as possible to minimize dosage and 2) with a minimum of sharp edges or protrusions. Also, another desirable feature of such an improved fastener would be a fastener configuration that did not form, or contribute to the formation of, pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide a simple yet effective method for joining tissue portions together with such an improved fastener and to provide an instrument for applying such an improved fastener according to such a method. It would be desirable if the improved method could be effected with a variety of different embodiments of such an improved fastener by means of appropriate instruments.

SUMMARY OF THE INVENTION

An improved fastener is provided to hold together separated portions of mammalian tissue, such as are defined by a wound or incision, to facilitate healing of the wound or incision. The fastener comprises an open loop fastening member which has a pair of legs adapted to penetrate two overlapped tissue portions and which has a link connecting the legs. The link is adapted to lie substantially against one of the tissue portions A receiver is provided for being disposed against the other of the tissue portions opposite the fastening member and has means for receiving the fastening member legs after the legs have been inserted through the tissue portions.

At least a portion of each of the legs or at least a portion of the receiver consists of material that is initially deformable under the application of pressure via a tool or instrument to effect engagement of the fastening member legs and receiver after the tissue portions have been penetrated by the fastening member legs and after the legs have been received in the receiver.

According to the method for joining tissue portions with the fastener, the two tissue portions are first approximated in a generally face-to-face relationship. Next, the fastening member is positioned on one side of the tissue portions with the legs oriented at an appropriate angle to penetrate the tissue portions. The receiver is positioned on the other side of the tissue portions opposite the fastening member and generally in alignment with the fastening member legs.

Relative movement is then effected between the fastening member on the one hand and the tissue portions and receiver on the other hand to cause penetration of the tissue portions by the fastening member legs and to cause a portion of each of the fastening member legs to be received within the receiver. The relative movement is effected until the link is disposed against the surface of one of the tissue portions and until the receiver is disposed against the other of the tissue portions.

Finally, deformation of the fastening member legs or of the receiver or deformation of both the receiver and the fastening member legs is effected with a tool or instrument so as to provide engagement of the fastening member legs and receiver.

A tool or instrument for applying at least one fastener to hold together the separated portions of the mammalian tissue in accordance with the above-described method preferably includes a first jaw for holding the fastening member on one side of the tissue portions with the legs oriented in an appropriate angle to penetrate the tissue portions. The instrument also includes a second jaw for holding the receiver on the other side of the tissue portions. opposite the fastening member and generally in alignment with the fastening member legs.

The instrument further includes means for moving the first and second jaws between (1) an open position for receiving the tissue portions between them and (2) a position in which the jaws are at least partially closed. Means are also provided on the instrument for moving the fastening member relative to the first jaw to penetrate the tissue portions with the legs of the fastening member and to locate at least portions of the legs of the fastening member within the receiver in the second jaw.

Additionally, the instrument is provided with a deforming member moveable relative to the second jaw for being urged against the fastening member legs, the receiver, or both so as to deform the fastening member legs, the receiver, or both for thus effecting an engagement of the fastening member legs and receiver. The deforming member is preferably moved by a suitable mechanism in response to movement of the first and second jaws to at least a partially closed position.

Numerous other features of (1) various embodiments of a novel tissue fastener, (2) of methods for applying such embodiments of the tissue fastener, and (3) of embodiments of an instrument for applying the tissue fastener in accordance with such methods will be apparent from the following detailed description and accompanying drawings.

BRIEF DESCRIPTION OF THE DRAWINGS

In the accompanying drawings forming part of the specification, and in which like numerals are employed to desginate like parts throughout the same.

DESCRIPTION OF THE PREFERRED EMBODIMENT

This invention may be used in many different forms. The specification and the accompanying drawings disclose only a few specific forms as an example of the use of the invention. The precise shapes and sizes of the components herein described are not essential to the invention unless otherwise indicated. The invention is not intended to be limited to the embodiments illustrated, and the scope of the invention will be pointed out in the appended claims.

THE FASTENER: FIRST EMBODIMENT

A first embodiment of the fastener is illustrated in an assembled configuration in FIGS. 1-4 and is generally indicated therein by reference numeral 50. Individual parts of the fastener are shown in FIGS. 5-9.

Figure 1:
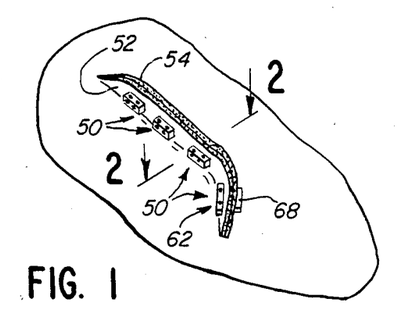
FIG. 1 is a fragmentary, perspective view of two portions of mammalian tissue defined by an incision or wound and being held together by a plurality of novel fasteners.

The plurality of such fasteners 50 are illustrated in FIG. 1 as holding together separated portions 52 and 54 of mammalian tissue, such as are defined by a wound or incision, to facilitate healing of the wound or incision.

Figure 2:
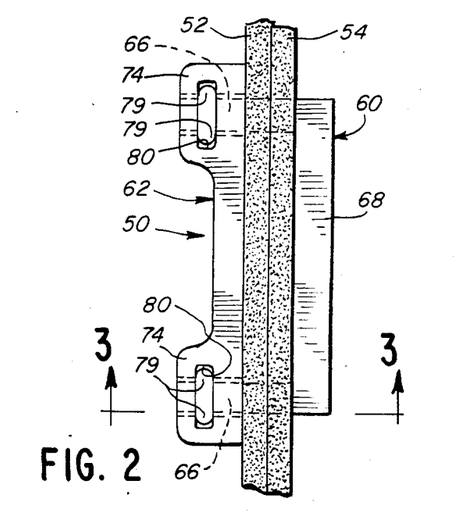
FIG. 2 is a greatly enlarged, fragmentary, cross-sectional view taken generally along the plane 2—2 in FIG. 1.
Figure 3:
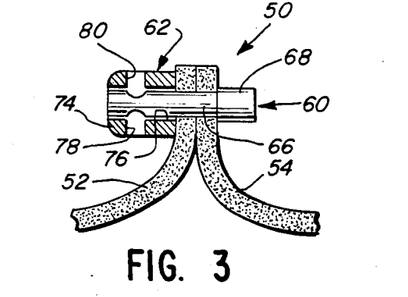
FIG. 3 is a fragmentary, cross-sectional view taken generally along the plane 3—3 in FIG. 2.
Figure 4:
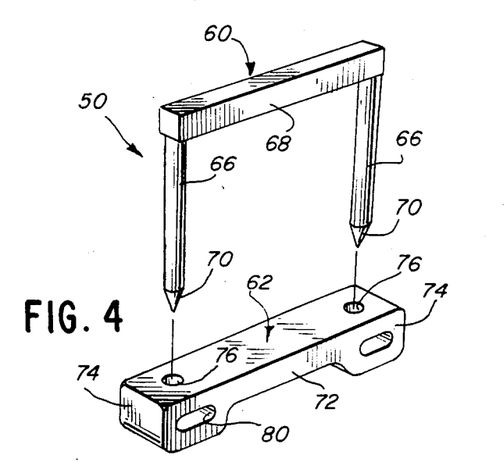
FIG. 4 is an exploded, perspective view of a first embodiment of the fastener shown in FIG. 1.
Figure 5:
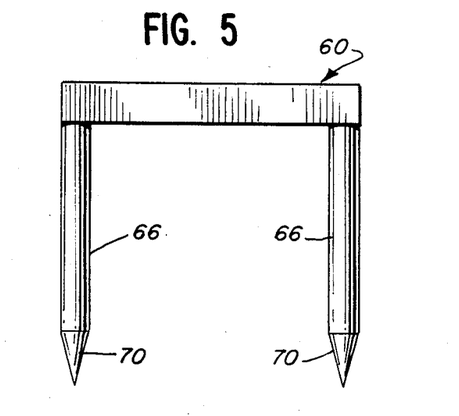
FIG. 5 is a side view of the fastening member of the fastener illustrated in FIG. 4.
Figure 6:
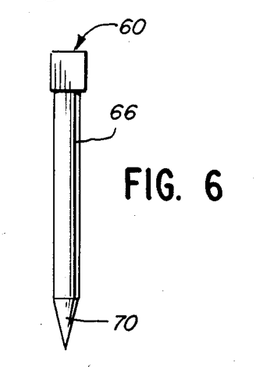
FIG. 6 is an end view of the fastening member of the fastener illustrated in FIG. 4.

The fastener includes two components, a generally U-shaped or open loop fastening member 60 and a receiver 62 which are initially separated as illustrated in FIG. 4 which are adapted to cooperate to compress or hold between them the tissue portions 52 and 54 as illustrated in FIGS. 1-3.

As is best illustrated in FIG. 4, the fastening member 60 includes (1) a pair of legs 66 adapted to penetrate the tissue portions and (2) a link 68 which is connected to the legs 66 and which is adapted to lie substantially against one of the tissue portions (e.g., tissue portion 54 in FIG. 2). The legs 66 of the fastening member are generally parallel to each other and are generally perpendicular to the link 68. Preferably, each leg 66 has a solid, generally cylindrical configuration with a conical end 70 (FIGS. 4-6) to facilitate or aid in the penetration of the tissue portions. The link 68 may have the regular parallelpiped shape illustrated or may have any other suitable shape.

Figure 7:
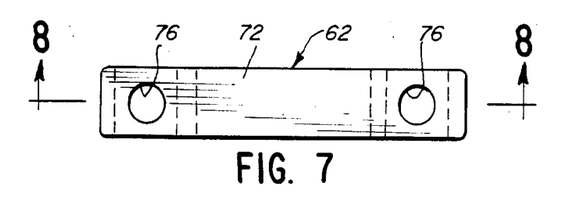
FIG. 7 is a top plane view of the receiver of the fastener illustrated in FIG. 4.
Figure 8:
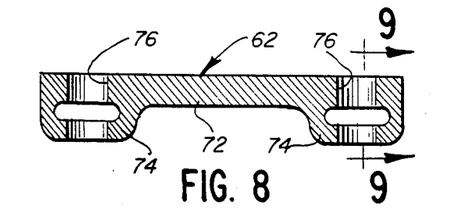
FIG. 8 is a cross-sectional view taken generally along the plane 8—8 and FIG. 7.
Figure 9:
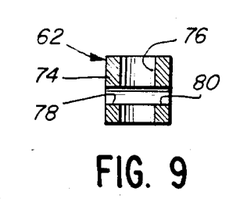
FIG. 9 is a cross-sectional view taken generally along the plane 9—9 in FIG. 8.

As best illustrated in FIGS. 7-9, the receiver 62 includes a central member 72 joining a pair of leg receiving members 74. Each leg receiving member 74 defines at least one passage 76 for receiving one of the fastening member legs 66 as best illustrated in FIG. 3. If the fastening member legs 66 have a cylindrical configuration as illustrated, then the receiving member passages 76 are preferably cylindrical bores of sufficient diameter to permit the legs 66 to be received (loosely or in sliding engagement). Each receiving member 74 and the passage 76 defined therein cooperate as means for receiving and encompassing at least a portion of one of the fastening member legs 66 after the leg has been inserted through the tissue portions as best illustrated in FIGS. 2 and 3.

Preferably, each receiving member 74 of the receiver 62 defines a first aperture 78 (FIGS. 3 and 9) communicating from the exterior of the receiving member 74 with the interior of the passage 76. Also, a second aperture 80 (FIGS. 3 and 9) is provided in the receiving member 74 opposite the first aperture 78 for communicating between the exterior of the receiving member 74 and the interior of the passage 76. At least one of these two apertures 78 and 80 is intended to accommodate the insertion of a ram-like member of a tool or instrument for deforming the fastening member leg 66 in a manner described in detail hereinafter. The other of the apertures 78 and 80 may function to position the receiver 62 within the instrument in a manner also described in detail hereinafter.

The fastening member 60 and the receiver 62 may be formed from suitable materials, such as thermoplastic polymer materials that are absorbable by mammalian tissue. For example, the fastening member 60 has been satisfactorily molded from a copolymer of lactide and glycolide. Preferably, the fastening member 60 is molded in a heated mold, is post-scoured, and is annealed.

METHOD FOR APPLYING THE FASTENER

According to the novel method of joining tissue portions with the above-described fastener 50, the tissue portions 52 and 54 (FIGS. 1-3) are approximated in surface-to-surface relationship. The fastening member 60 is then positioned on one side of the tissue portions with the legs 66 oriented at an appropriate angle to penetrate the tissue portions. The receiver 62 is held on the other side of the tissue portions opposite the fastening member 60 and generally in alignment with the fastening member legs 66. Specifically, the passages 76 are aligned with the fastening member legs 66.

Next, relative movement between the fastening member 60 and the receiver 62 is effected to urge the fastening member and the receiver closer together to cause the fastening member legs 66 to penetrate the tissue portions 52 and 54 and to locate at least portions of the fastening member legs 66 within the receiver 62. The relative movement between the fastening member 60 and the receiver 62 is terminated when the fastening member link 68 is at a desired distance from the receiver 62 to secure the tissue portions together. Preferably, this movement is terminated after the tissue portions have been compressed together a desired amount.

At this point, the distal ends of the fastening member legs 66 will typically protrude from the receiver opposite the side of the receiver that is contacting one of the tissue portions. In FIGS. 1-2, the legs 66 are not shown protruding beyond the receiver 62 since, in accordance with a preferred further step of the method, the protruding portions have been severed flush with the receiver 62. An instrument for applying the fastener 50 and severing the legs 66 are described in detail hereinafter. However, in its broadest form, the method of applying the fastener 50 to the tissue portions does not necessarily require the severance of the protruding portions of the fastening member legs 66.

Regardless of whether or not the protruding portions of the fastening member legs 66 are severed, the fastening member legs 66 and/or the receiver 62 are acted upon in a certain manner to effect an engagement of the legs 66 with the receiver 62 to hold the two tissue portions together. To this end, in a preferred form of the method, each fastening member leg 66 is deformed or coined to force a bulged out portion 79 of each fastening member leg 66 into engagement with the receiver 62.

Specifically, as best illustrated in FIGS. 2 and 3, a force may be applied by means of a tool or instrument through one or both of the apertures 78 and 80 in the receiver 62 and against a portion of each leg 66. The amount of force is such that the pressure on each leg 66 deforms a portion 79 of the leg material outwardly into either end of one or both of the apertures 78 and 80 as is best illustrated in FIG. 2.

To accommodate this bulging out of the leg portion 79, the apertures 78 and 80 have a dimension (measured normal to longitudinal axis of the passage 76) that is greater than the dimension of the passage 76 (measured normal to the longitudinal axis of the passage). In the embodiment illustrated in the FIGS. 1-9, the apertures 78 and 80, when viewed from the side, are seen to each have a generally right rectangular configuration (with somewhat rounded corners) with a length greater than the diameter of the cylindrical bore passage 76. This accommodates the bulged out portion 79 of the fastening member leg material and thus effects a rivet-like engagement of the leg 66 with the receiver 62.

It has been found that the above-described method of applying the fastener 50 to the tissue portions results in a relatively strong retention structure comprising the fastening member 60 and engaged receiver 62. Further, one size fastener 50 may be used for a variety of different tissue thicknesses since the fastening member 60 can be inserted into the receiver 62 to the desired depth and the legs 66 can then be deformed to effect the engagement of the legs and receiver with the desired amount of tissue compression. This deformation can take place at any point along the length of each leg 66, depending on tissue thickness. Such a fastener structure and method of applying the fastener readily accommodate application of the fastener 50 by means of a suitable instrument that can be designed to apply a plurality of such fasteners simultaneously.

With the embodiment of the fastener 50 described above, the legs 66 are deformed into engagement with the receiver 62. However, it is to be understood that the legs 66 may be formed with apertures or notches (not illustrated) and that portions of the receiver 62 may be deformed into the leg notches or apertures for effecting the engagement between the receiver 62 and fastening member 60. Further, a combination of both the deformation of the receiver 62 and the deformation of the legs 66 may also be used to effect engagement of the receiver 62 and fastening member 60.

With the above-described method, the protruding portions of the fastening member legs 66 may be severed during or after the step of deforming the legs 66 and/or receiver 62. Preferably, during the step of severing the protruding portions of the fastening member legs 66, the protruding portions of the fastening member legs are surrounded with a suitable container for catching the leg protruding portions after they are severed so as to prevent the severed portions of legs from falling into the surrounding tissue or body cavity.

The material from which the fastening member legs 66 are formed is preferably selected to accommodate the deforming action. To this end, copolymers of lactide and glycolide have been found to work satisfactorily. If just the legs are to be deformed, the receiver 62 need not be fabricated from such a relatively easily deformable matetial. On the other hand, the copolymers of lactide and glycolide may be made relatively inelastic enough to function well as a receiver also even if it is not intended that the receiver be deformed.

Regardless of the materials selected for the fastening member 60 and receiver 62, it may be desirable to effect the method of deforming the fastening legs 66 and/or receiver 62 with the aid of heat to soften the material. Such heat may be provided by a suitable process (e.g., electrical resistance heating). Such heating would reduce the magnitude of the mechanical forces required to effect the necessary deformation.

FASTENER APPLIER INSTRUMENT

Figure 10:
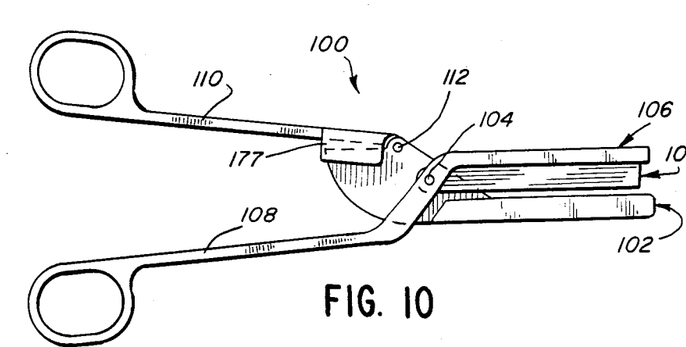
FIG. 10 is a side view of an instrument for applying the first embodiment of the fastener illustrated in FIGS. 1-9.
Figure 11:
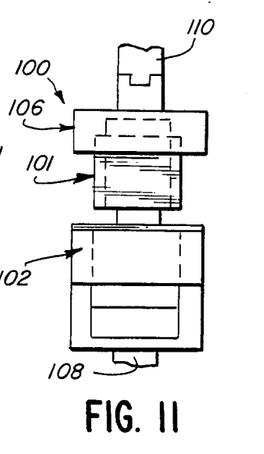
FIG. 11 is a greatly enlarged, fragmentary, front end view of the instrument illustrated in FIG. 10.
Figure 12:
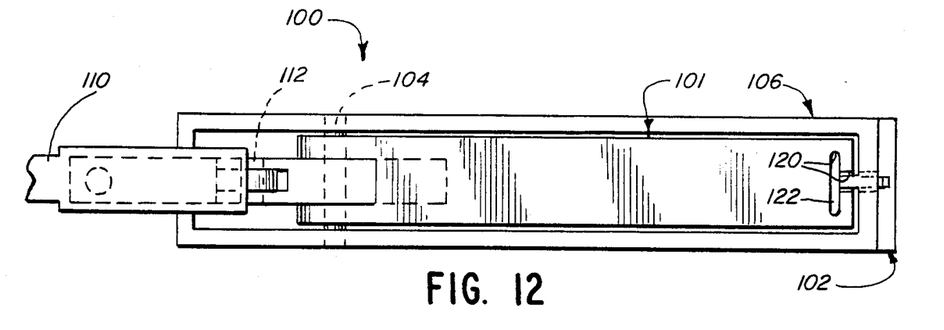
FIG. 12 is a greatly enlarged, fragmentary, top plane view of the instrument of FIG. 10.

A tool or instrument for applying the first embodiment of the fastener 50 is illustrated in FIGS. 10-19 and is designated generally by the reference numeral 100. As is best illustrated in FIGS. 10, 11, and 12, the instrument includes a first jaw 101 for holding the fastening member 60 on one side of the tissue portions with the fastening member legs 66 oriented at an appropriate angle to penetrate the tissue portions 52 and 54. The instrument 100 further includes a second jaw 102 for holding the receiver 62 on the other side of the tissue portions opposite the fastening member 60 and generally in alignment with the fastening member legs 66.

The first jaw 101 and second jaw 102 are pivotally mounted together about a pin 104. Also pivotally mounted to pin 104 is a fastening member driving frame 106 which functions as a means for moving the fastening member 60 relative to the first jaw 101 to penetrate the tissue portions 52 and 54 with the legs 66 of the fastening member and to locate at least portions of the fastening member legs 66 within the receiver 62 held in the second jaw 102.

Figure 16:
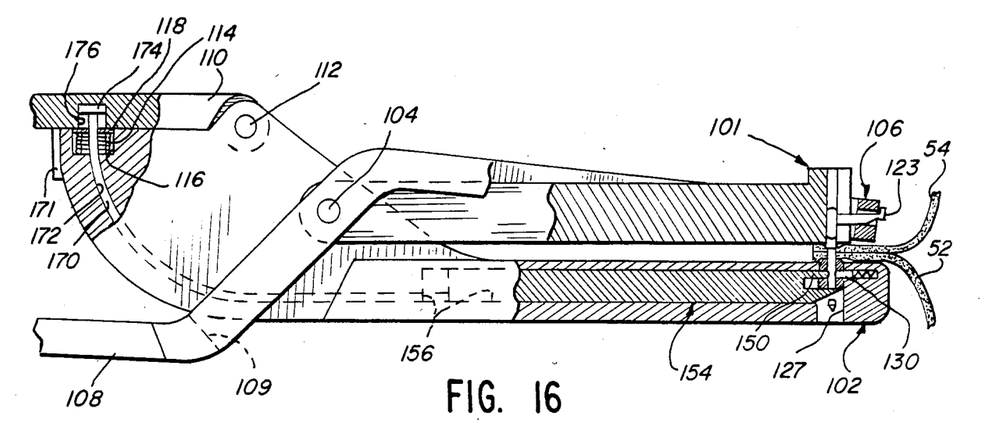

A first scissors-type handle lever 108 extends rearwardly from the driving frame 106. Therefore, the fastening member moving means or driving frame 106 can be regarded as being mounted to, and extending forwardly from, the first handle lever 108. The first handle lever 108 defines a "Y" configuration where it is joined to the driving frame 106. At this point, the front end of the handle lever 108 defines an engaging surface 109 for engaging the lower exterior portion of the second jaw 102 when the jaws 101 and 102 are closed (FIG. 16).

A second scissors-type handle 110 is pivotally mounted about a pin 112 to the upper rear portion of the second jaw 102. The second jaw 102 can be alternatively regarded as being pivotally mounted to, and extending from, the second handle lever 110. Both handle levers 108 and 110 are adapted for relative movement toward and away from each other.

Figure 13:
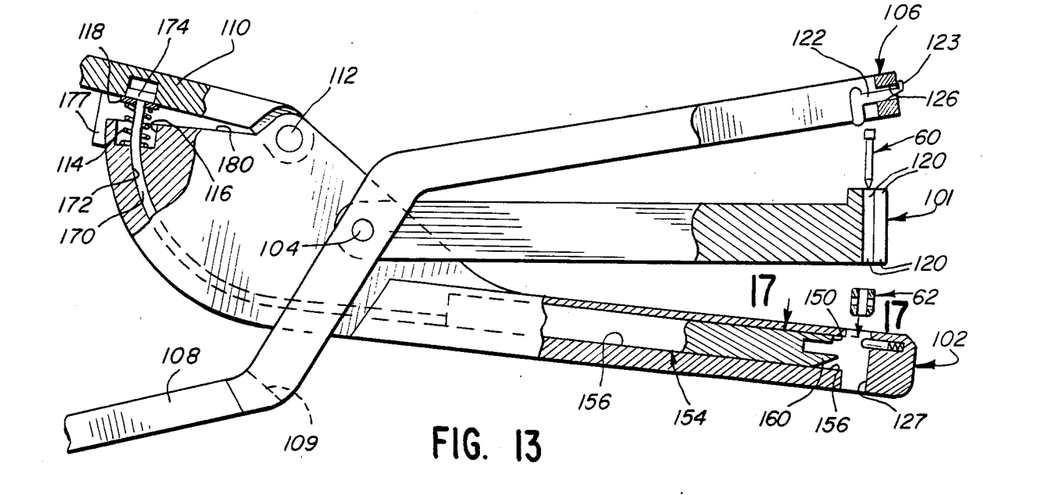
FIGS. 13-16 are greatly enlarged, fragmentary, partial cross-sectional views of the instrument of FIG. 10 illustrating the sequence of operation of the instrument.

As best illustrated in FIG. 13, the second handle lever 110 is biased outwardly from the first handle lever 108 by means of a helical compression spring 114 (FIG. 13). The spring 114 is disposed within a bore 116 in the upper rear portion of the second jaw 102 and bears upwardly against an annular bearing ring or plate 118 which is secured to the underside of the second handle lever 110.

Figure 14:
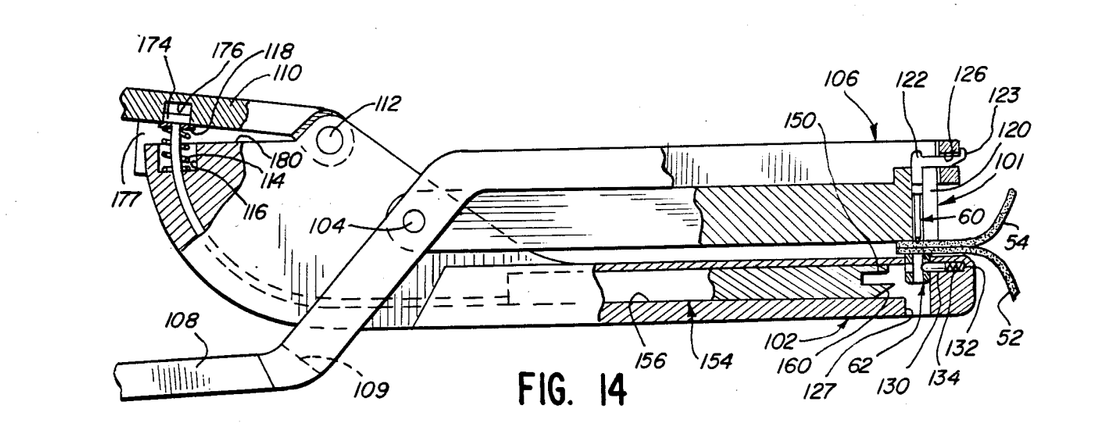

As best illustrated in FIG. 13, the first jaw 101 is mounted to the pin 104 in the manner that permits the first jaw 101 to move relative to both the fastening member driving frame 106 and the second jaw 102. The first jaw 101 is adapted to cooperate with the fastening member driving frame 106 as best illustrated in FIGS. 12 and 14. Specifically, the front end of the jaw 101 defines a passage in the form of a T-shaped slot 120 for receiving the fastening member 60 for receiving a generally T-shaped pusher member 122.

Figures 17, 18, 19:
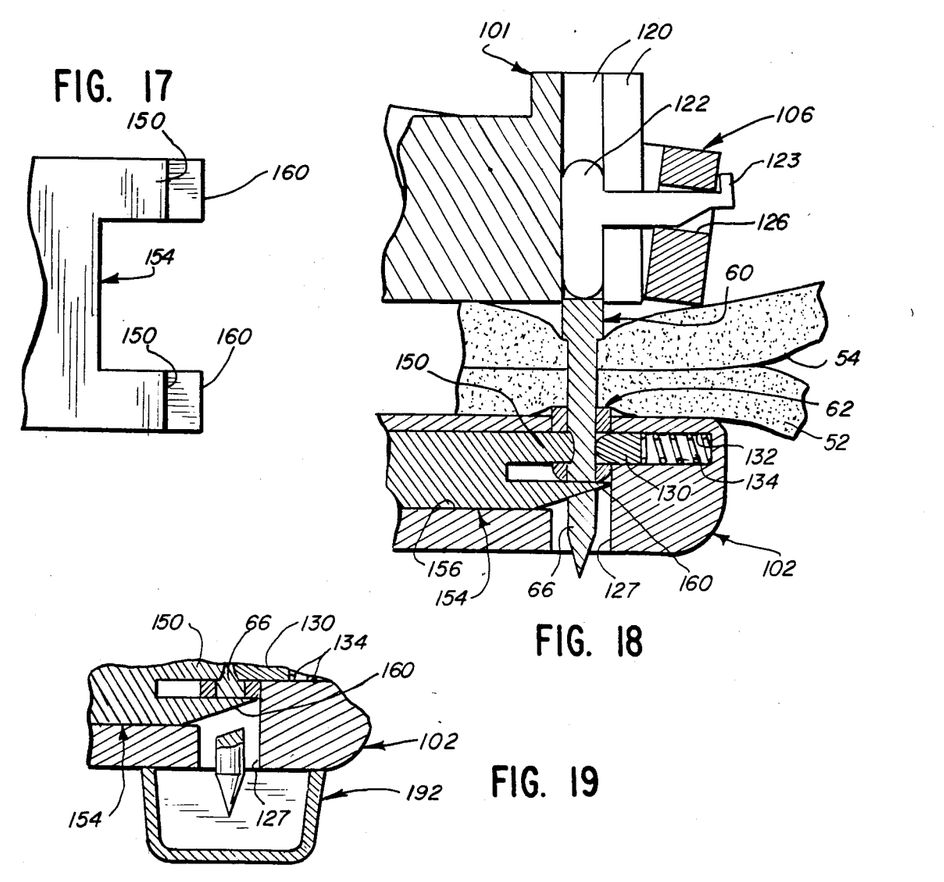
FIG. 17 is a greatly enlarged, fragmentary plane view of the instrument lower jaw taken along the plane 17—17 in FIG. 13.
FIG. 18 is a greatly enlarged, fragmentary, cross-sectional view of the front end of the jaws of the instrument in the closed position shown in FIG. 16.
FIG. 19 is a fragmentary, cross-sectional view similar to FIG. 18 but limited to the end of the lower jaw and showing a modified form of the instrument.

As best illustrated in FIGS. 13 and 14, the crosswise portion of the T-shaped slot or passage 120 functions as a channel for frictionally receiving the fastening member 60 and the cross bar portion of the pusher member 122. The base of the pusher member 122 extends out of the slot 120 and is slidably disposed within an aperture 126 at the front of the fastening member driving frame 106 as best illustrated in FIG. 18. This mounting of the pusher member 122 in the frame 106 facilitates entry of the pusher member 122 into the T-shaped slot 120 of the first jaw 101.

The pusher member 122 preferably includes an upwardly projecting tab 123 (FIG. 13) to retain the pusher member 122 within the fastening member driving frame 106 when the frame 106 is tilted upwardly in the orientation shown in FIG. 13.

The second jaw 102 holds the fastener receiver 62 in a slot 127 as best illustrated in FIG. 14 and houses the fastening member leg deforming and severing mechanism as is next explained in detail. The lower jaw 102 includes a generally cylindrical anvil member 130 slidably disposed within a cylindrical bore 132 and biased outwardly a predetermined amount by means of a helical spring 134. The distal end of the anvil 130 has a curved or somewhat hemispherical configuration adapted to enter into one of the receiver apertures 78 or 80 (FIG. 9) to vertically position the receiver 62 within the second jaw 102. Lateral positioning of the receiver 62 in the second jaw 102 is effected by the four walls defining the slot 127 in the lower jaw 102.

To accommodate the insertion of the receiver 62 into the second jaw 102, the bottom of the receiver 62 is preferably rounded so as to tangentially engage the hemispherical end of the anvil member 130 and cause the anvil member 130 to be pushed rearwardly against the spring 134 until the receiver apertures 78 and 80 are aligned with the anvil member 130. At this point, the anvil member 130 is biased outwardly into one of the receiver apertures to fix the vertical position of the receiver 62 in the second jaw 102.

As best illustrated in FIGS. 13, 17, and 18, a pair of deforming members 150 are mounted for movement within the second jaw 102. Preferably, as best illustrated in FIGS. 13-17, the deforming members 150 are part of a unitary reciprocative actuating member 154 which is slidably disposed in a receiving cavity 156 (FIGS. 16 and 18) in the second jaw 102.

Also unitary with the reciprocative actuating member 154 are two cutting blades 160 which are spaced below, and in alignment with, the deforming members 150.

A novel means is provided for moving the deforming members 150 and the cutting blades 160 forwardly into the fastener. Specifically, the reciprocative actuating member 154 includes a flexible drive member 170 extending rearwardly in an arcuate channel 172 in the second jaw 102. The flexible drive member 170 includes a disk 174 at its distal end which is received in a cylindrical bore 176 defined in the second handle lever 110.

Normally, when the handle levers 108 and 110 are in the unactuated, open position illustrated in FIG. 13, the spring 114 biases the handle levers 108 and 110 apart so that the annular ring 118 secured to the second handle lever 110 pulls up on the disk 174, and hence pulls the attached flexible drive member 170 upwardly and rearwardly relative to the front of the instrument. This causes the reciprocative actuating member 154 to be pulled rearwardly in its receiving cavity 156 to the fully retracted position illustrated in FIG. 13.

On the other hand, when the handle levers 108 and 110 are closed in the orientation illustrated in FIG. 16, disk 174 is moved downwardly by the second handle lever 110 to force the drive member 170, and hence the actuating member 154, forwardly to the extended position illustrated in FIGS. 16 and 18. The resulting action of the deforming members 150 and blades 160 on the fastener is described in detail hereinafter.

As best illustrated in FIG. 13, the second handle lever 110 is preferably provided with a pair of depending skirts 177 (one of which is visible in FIG. 10 and the other of which is visible in FIG. 13) to inhibit access to the flexible drive member 170 and spring 114. Also, as best illustrated in FIG. 13, the upper rear portion of the second jaw 102 defines a flat abutment surface 180 between the skirts 177 for cooperating with the underside of the second handle lever 110 to limit the movement of the second handle lever 110 relative to the second jaw 102 and, hence, relative to the first handle lever 108. This, of course, limits the forward travel of the reciprocative actuating member 154 to the positon illustrated in FIG. 16.

In operation, the tool is initially oriented as illustrated in FIG. 13 with the first jaw 101 and the second jaw 102 temporarily held apart to permit the insertion of the receiver 62 into the slot 127 of the lower jaw 102. When properly inserted, the receiver is engaged as described above by the anvil member 130.

Next, the fastening member 60 is inserted in the driving frame channel 120 as illustrated in FIGS. 13 and 14. Then, as illustrated in FIG. 14, the first jaw 101 and the second jaw 102 are disposed on either side of the tissue portions 52 and 54 that have been approximated in surface-to-surface relationship. The first handle lever 108 is pulled toward the second handle lever 110 to bring the pusher member 122 on top of the fastening member 60 and into the channel 120. Initially, the second handle lever 110 does not pivot relative to the second jaw 102 because the force applied to the handle lever 110 is not great enough to overcome the force of spring 114. Consequently, relative movement occurs between the driving frame 106 and the second jaw 102 so that the pusher member 122 forces the fastening member 60 through the tissue portions 52 and 54 and into the receiver 62.

Figure 15:
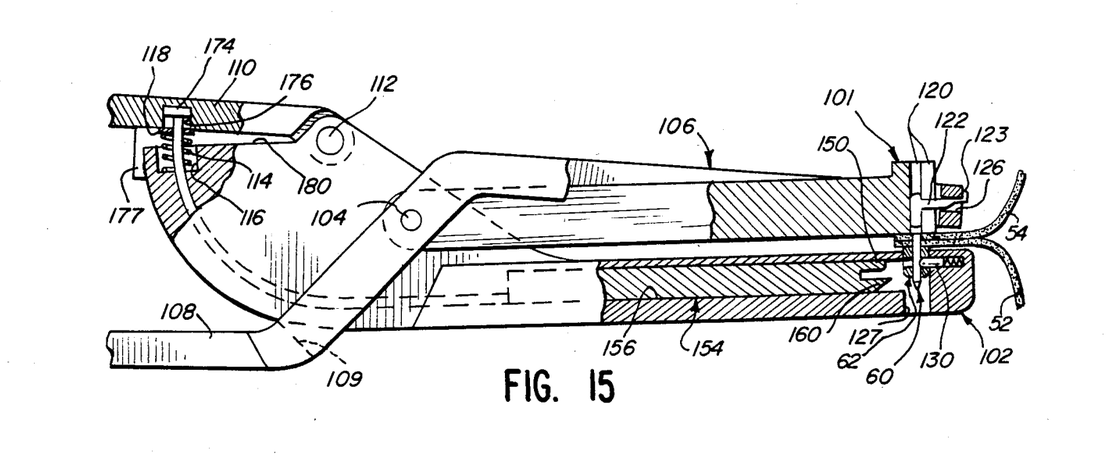

In the instrument embodiment illustrated in FIGS. 13–16, the downward movement of the pusher member 122 terminates when the driving frame 106 pivots to the orientation illustrated in FIG. 15. At this point, the engaging surface 109 of the first handle lever 108 engages the bottom exterior surface of the second jaw 102 and prevents a further pivoting of the frame 106 and second jaw 102 about the pin 104. This precludes undue compression of the tissue portions 52 and 54. However, it is to be realized that the engagement of the second jaw 102 by the first handle lever 108 may not be necessary in some situations and that no limitation of the downward movement of the pusher member 122 need necessarily be provided.

If the engaging surface 109 is provided on the handle 108 for engaging the second jaw 102, then further movement of the first handle lever 108 towards the second handle lever 110 is prohibited when the first handle lever 108 reaches the orientation illustrated in FIG. 15. At this point, any further force applied to squeeze the two together handle levers 108 and 110 acts to overcome the force of spring 114 and to cause the second handle lever 110 to pivot about the pin 112. This drives the reciprocative actuating member 154 forward to the position illustrated in FIG. 16.

When the second handle lever 110 engages the top surface 180 of the rear portion of the second jaw 102, further forward movement of the reciprocative actuating member 154 is necessarily prevented. At this point, the deforming members 150 have become positioned within the apertures (78 or 80 in FIG. 9) of the receiving member 62 and have deformed a portion of each of the fastening member legs 66 to thereby effect an engagement of the fastening member legs 66 and receiver 62 in the manner described in detail above with respect to FIGS. 1–9.

Similarily, when the actuating member 154 is in the extended position as illustrated in FIG. 16, the spaced-apart cutting blades 160 have moved across the bottom of the receiver 62 to sever the protruding portions of the legs 66 from the fastening member 60 at substantially the same time the legs are being deformed into engagement with the receiver 62 by members 150. Preferably, the cutting blades 160 are arranged to sever the protruding portions of the legs flush with the bottom of the receiver so as to eliminate the possiblity of protrusions that could injure surrounding tissue.

Even if the engagement surface 109 is not provided as part of the first handle lever 108 and associated frame 106, the instrument 100 will function in the same manner as just described. Specifically, even though the downward movement of the pusher member 122 is not terminated by mechanical engagement of interacting parts of the instrument, the force required to compress the tissue portions 52 and 54 between the fastening member link 68 and the second jaw 102 eventually becomes so great that the spring 114 is overcome and the second handle 110 pivots to the position illustrated in FIG. 16 to effect the deformation of the fastening member legs 66 and the severance of the protruding portions of the legs.

If desired, the instrument 100 may be provided with means for heating the deforming members 150. Although not illustrated, such heating means could include electrical resistance heating elements powered by a suitable battery. Heating of the deforming members 150 would reduce the amount of force required to cause deformation of the fastener leg material.

After the fastener 50 has been applied as illustrated in FIG. 18, the handle levers 108 and 110 are opened. The second jaw 102 can be disengaged from the receiver 62 by pulling the second jaw 102 away from the receiver 62 (which is now secured to the tissue with the fastening member 60). It is possible to disengage the second jaw 102 from the receiver 62 because the curved distal end of the anvil 130 in the second jaw 102 will be forced further into the receiving cavity 132 and out of the receiver aperture as the second jaw 102 is pulled downwardly past the bottom of the receiver 62.

FIG. 19 illustrates a modification of the instrument 100 shown in FIGS. 10–18. Specifically, a cage, housing, or container 192 is provided at the bottom of the second jaw 102 for receiving the severed portions of the fastening member legs 66. This prevents the severed portions of the legs from falling into the body cavity. The housing 192 can be designed so it is readily movable from the second jaw 102 when desired for disposing of the severed leg portions.

Although the instrument 100 has been illustrated as being designed to deform the fastening member legs into engagement with the receiver substantially simultaneously with the step of severing the protruding ends of the legs, it is to be realized that the step of severing the legs may be effected before or after the deformation step.

Further, although the instrument 100 preferably includes the cutting blades 160 for severing the projecting portions of the legs 66 as described above, in some applications it may not be desired to sever the legs. In such applications, the cutting blades 160 may, of course, be omitted from the instrument if desired.

Although the instrument 100 has been illustrated as designed for applying one fastener at a time, it is to be realized that the instrument may be modified to apply a plurality of fasteners simultaneously. For example, the jaws could be made considerably wider and could be provided with a plurality of cavities 132 and passages 120 for holding the receivers 62 and fastening members 60, respectively, and with a plurality of pusher members 122

THE FASTENER: SECOND EMBODIMENT

The second embodiment of the fastener is illustrated in FIGS. 20–24 and is designated generally by the reference numeral 50A. The elements of the second embodiment 50A that are identical or functionally analogous to those of the first embodiment 50 are designated by reference numerals identical to those used for the first embodiment with the exception that the second embodiment reference numerals are followed by the upper case letter A whereas the first embodiment reference numerals are not followed by any letter.

The fastener 50A has an open loop or U-shaped fastening member 60A with legs 66A substantially identical to the fastening member 60 of the first embodiment described above with reference to FIGS. 1–9.

The fastener 50A also includes a receiver 62A which is similar to the receiver 62 of the first embodiment of the fastener 50 described above with reference to FIGS. 1–9. The receiver 62A has central member 72A joining a pair of leg receiving members 74A. Each leg receiving member 74A defines a generally cylindrical bore 76A for receiving one of the fastening member legs 66A.

Figures 20, 21, 22, 23, 24:
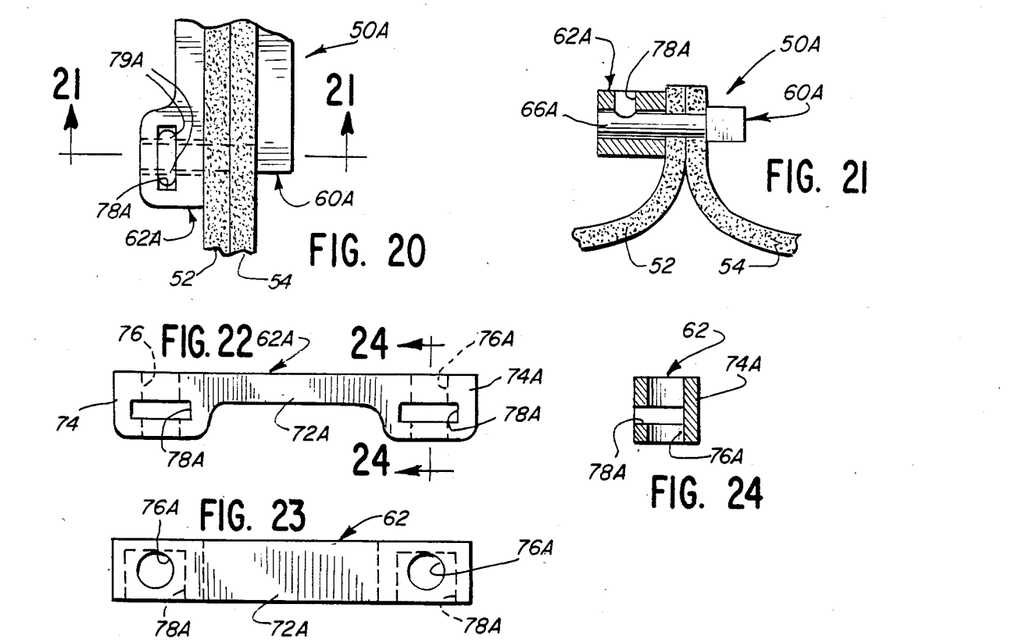
FIG. 20 is a fragmentary, partial, cross-sectional view of a second embodiment of the fastener shown in an orientation similar to that of the orientation of the first embodiment of the fastener in FIG. 2.
FIG. 21 is a fragmentary, cross-sectional view taken generally along the plane 21—21 in FIG. 20.
FIG. 22 is a side view of the receiver of the second embodiment of the fastener shown in FIGS. 20 and 21.
FIG. 23 is a top plane view of the receiver of the second embodiment of the fastener of FIGS. 20-22.
FIG. 24 is a cross-sectional view taken generally along the plane 24—24 in FIG. 22.
Figure 25:
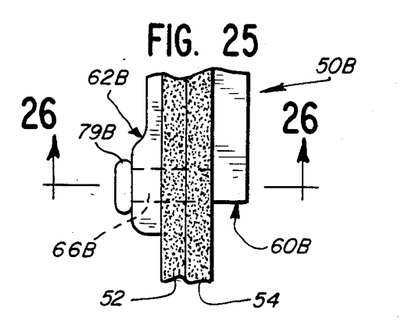
FIG. 25 is a fragmentary, partial, cross-sectional view of a third emhodiment of the fastener shown in an orientation similar to that of the orientation of the first embodiment of the fastener in FIG. 2.
Figure 26:
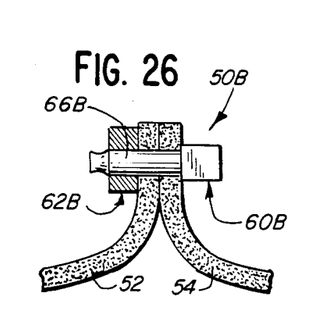
FIG. 26 is a fragmentary, cross-sectional view taken generally along the plane 26—26 in FIG. 25.
Figure 27:
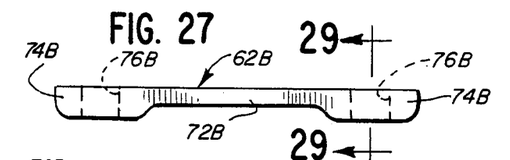
FIG. 27 is a side view of the receiver of the third embodiment of the fastener of FIGS. 25 and 26.
Figure 28:
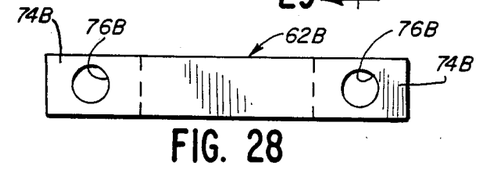
FIG. 28 is a top plane view of the third fastener embodiment receiver of FIGS. 25-27.
Figure 29:
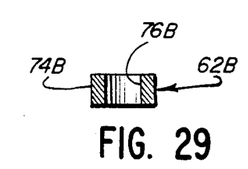
FIG. 29 is a cross-sectional view taken generally along the plane 29—29 in FIG. 27.

Further, each receiving member 74A defines one aperture 78A communicating between the exterior of the receiving member and the interior of the bore 76A. Unlike the receiver 62 of the first embodiment of the fastener 50 described above with reference to FIGS. 1–9, the receiver 62A does not have a second aperture opposite the aperture 78A. The aperture 78A functions to admit a deforming member of a suitable instrument that is used in applying the fastener 50A to tissue portions. The deforming member of the instrument would pass through the aperture 78A and deform the leg 66A to produce a bulged out portion 79A (FIG. 20). To accommodate the bulged out portion 79A, the aperture 78A has a dimension (as measured in the direction normal to the longitudinal axis of the fastening member leg) which is larger than the diameter of the leg receiving bore 76A. Thus, the bulged out portion 79A acts to retain the fastening member 60A in the receiver 62A.

The second embodiment of the fastening member 50A may be applied with a suitable instrument similar to the instrument 100 described above with reference to FIGS. 10–19. However, such an instrument would not require the spring biased anvil (anvil 130 illustrated in FIG. 18). Other suitable means for temporarily aligning the receiver 62A vertically within the instrument lower jaw would be provided.

THE FASTENER: THIRD EMBODIMENT

A third embodiment of the fastener is illustrated in FIGS. 25–29 wherein the fastener is designated generally by reference numeral 50B. The elements of the third embodiment of the fastener 50B that are identical or functionally anaglous to those of the first embodiment of the fastener 50 are designated by reference numerals identical to those used for the first embodiment with the exception that the third embodiment reference numerals are followed by the upper case letter B whereas no letter follows the first embodiment reference numerals.

The third embodiment of the fastening member 50B includes a generally U-shaped fastening member 60B that is substantially identical, in the unapplied condition, to the fastening member 60 of the first embodiment of the fastener 50 described above with reference to FIGS. 1–9. The third embodiment of the fastener 50B also includes a receiver 62B that includes a central member 72B joining a pair of leg receiving members 74B. Each leg receiving member 74B defines at least one passage, such as a cylindrical bore 76, for receiving one of the fastening member legs 66B.

The height of each leg receiving member 74B is less than the height of each leg receiving member 74 of the first embodiment of the fastener 50 described above with reference to FIGS. 1-9. Further, no apertures (such as apertures 78 and 80 in the receiver 62 of the first embodiment of the fastener 50 illustrated in FIGS. 1-4) are provided. Rather, the legs 66B are deformed, as by producing a bulge 79B (FIG. 25), adjacent the side of the receiver 62B that faces away from the tissue portion 52 and 54.

The deformation of the fastening member legs 66B may be effected with a instrument similar to the instrument 100 described above with reference to FIGS. 10-19. However, the spring biased anvil 130 of the instrument 100 (FIG. 18) need not be provided. Rather, a fixed anvil may be provided in such an instrument immediately below the bottom of the receiver. In addition, the cutter blades (such as cutter blades 160 of the instrument 100 illustrated in FIG. 18) would be spaced below the bottom of the receiver 62B by an amount sufficient to accommodate the deformed portion 79B of the fastening member legs.

THE FASTENER: FOURTH EMBODIMENT

Although not illustrated, the fastener design may also include an interference fit or friction fit feature. For example, the fastening member legs may be provided with protrusions for engaging suitable portions of the receiver. The friction fit would provide a retention restraint in addition to the restraint provided by the permanent deformation of the legs and/or receiver.

ALTERNATIVE DESIGN FEATURES

In the figures, the two legs of the fastening member are connected by a portion of the fastening member (e.g., the link or clamping member) which is illustrated as being generally straight and extending perpendicular to the two legs. The structure need not be limited to such a shape however. Instead, all or a portion of the length of the fastening member between the two legs may be arched or arcuate or may include an arcuate portion (e.g., an inverted U-shaped configuration). This would function to initially provide a free space between the upper tissue portion and the top of the fastening member to allow for some expansion of the tissue.

However, in those situations where increased initial tissue compression is desired, a modified receiver structure may be provided to cooperate with the above-described arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

From the foregoing, it will be observed that numerous variations and modifications may be effected without departing from the true spirt and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A method for applying at least one fastener to hold together separated portions of mammalian tissue, such as are defined by a wound or incision, to facilitate healing of the wound or incision, wherein said fastener includes an open loop fastening member that comprises a pair of legs adapted to penetrate said tissue portions and a link connected to said legs that is adapted to lie substantially against one of said tissue portions, and wherein said fastener further includes a receiver that is adapted to be disposed against the other of said tissue portions opposite said fastening member, said receiver defining a pair of spaced-apart passages for receiving the legs of the fastening member, and said receiver defines at least two apertures with each said aperture communicating from the exterior of said receiver with the interior of one of said receiver passages, said method comprising the following steps:

approximating said tissue portions in surface-to-surface relationship;

positioning said fastening member on one side of said tissue portions with said legs oriented at an appropriate angle to penetrate said tissue portions;

holding said receiver on said other side of said tissue portions opposite said fastening member and generally in alignment with said fastening member legs;

effecting relative movement between said fastening member and said receiver to urge said fastening member and said receiver closer together to cause said fastening member legs to penetrate said tissue portions and to locate at least portions of said fastening member legs within the passages of said receiver;

terminating said step of effecting relative movement between said fastening member and said receiver when said fastening member link is at a desired distance from said receiver to secure said tissue portions together; and deforming said fastening member legs by forcing a tool or instrument into each of said apertures against said leg to deform a portion of each leg and effect engagement of the fastening member legs and receiver.

2. The method in accordance with claim 1 in which a first aperture in said receiver communicates from the exterior of said receiver with the interior of one of said receiver passages; and a second aperture opposite the first aperture and communicates from the exterior of said receiver with the interior of said one receiver passage; and wherein said deforming step includes moving an anvil member of said tool into said second aperture against one of said fastening member legs and moving a deforming member of said tool into said first aperture against said one fastening member leg to effect deformation of said one leg.

3. The method in accordance with claim 1 in which said method includes the further step, during or after said deforming step, of severing the protruding portions of the fastening member legs from the receiver flush with said receiver second side.

4. The method in accordance with claim 3 further including the step, during the step of severing the protruding portions of said fastening member legs, of surrounding the fastening member leg protruding portions with a container for catching the leg protruding portions after they are severed so as to prevent the severed protruding portions of the legs from falling into the surrounding tissue.

5. A fastener adapted to hold together separated portions of mammalian tissue, such as are defined by a wound or incision, to facilitate healing of the wound or incision, said fastener comprising:
- an open loop fastening member, said fastening member comprising a pair of legs adapted to penetrate said tissue portions and a link connecting said legs that is adapted to lie substantially against one of said tissue portions;
- a receiver adapted to be disposed against the other of said tissue portions opposite said fastening member, said receiver having means for receiving said fastening member legs after said legs have been inserted through said tissue portions, said receiver means including at least one passage in said receiver for receiving one of said fastening member legs, said receiver including a first aperture communicating from the exterior of the receiver with the interior of said passage and a second aperture opposite the first aperture communicating from the exterior of the receiver with the interior of said passage,
- at least a portion of said legs consisting of a material that is initially deformable under the application of a predetermined amount of pressure to effect engagement of the fastening member legs and receiver after the tissue portions have been penetrated by said fastening member legs and after said legs have been received in said receiver.

6. The fastener in accordance with claim 5 in which each said aperture has a generally right rectangular configuration.

7. An instrument for applying at least one fastener to hold together separated portions of mammalian tissue, such as are defined by a wound or incision, to facilitate healing of the wound or incision, said fastener including an open loop fastening member that comprises a pair of legs adapted to penetrate said tissue portions and a link connecting said legs that is adapted to lie substantially against one of said tissue portions, said fastener further including a receiver adapted to be disposed against the other of said tissue portions opposite said fastening member and adapted to accept the legs of the fastening member, said instrument comprising:
- a first jaw for holding said fastening member on one said of said tissue portions with said legs oriented at an appropriate angle to penetrate said tissue portions;
- a second jaw for holding said receiver on said other side of said tissue portions opposite said fastening member and generally in alignment with said fastening member legs;
- means for moving said first and second jaws between an open position for receiving said tissue portions therebetween and in at least a partially closed position;
- means for moving said fastening member relative to said first jaw to penetrate said tissue portions with the legs of said fastening member and to locate at least portions of said legs of said fastening member within said receiver in said second jaw;
- a deforming member movable relative to said second jaw member for being urged against the fastening member legs to thereby effect an engagement of the fastening member legs and receiver;
- means for moving said deforming member to effect said deformation; a cutting blade associated with said second jaw; and means for moving said blade relative to said second jaw adjacent said receiver to cut off portions of said fastening member legs extending beyond said receiver when said jaws are in said at least partially closed opposition.

8. The instrument in accordance with claim 7 in which said instrument is adapted to apply one fastener at a time and in which said instrument includes a reciprocative actuating member slidably disposed within said second jaw; in which said deforming member and said cutting blade are unitary with said reciprocative actuating member; in which said instrument includes a handle lever pivotally mounted to said second jaw; in which said instrument further includes handle lever biasing means for biasing said handle lever into a first position relative to said second jaw; and in which said actuating member includes a drive member adapted to be engaged by said handle lever when sufficient force is applied to said handle lever to overcome said handle lever biasing means and move said handle lever relative to said second jaw away from said open position for engaging said drive member to thereby move said actuating member relative to said second jaw to effect the deformation with said deforming member and the cutting off of said fastening member legs with said cutting blade.

* * * * *